(12) United States Patent
Wagle et al.

(10) Patent No.: US 6,596,744 B2
(45) Date of Patent: Jul. 22, 2003

(54) METHOD FOR TREATING FIBROTIC DISEASES OR OTHER INDICATIONS IIC

(75) Inventors: Dilip Wagle, New York, NY (US); Martin Gall, Morristown, NJ (US); Stanley C. Bell, Narberth, PA (US); Edmond J. LaVoie, Princeton Junction, NJ (US)

(73) Assignee: Alteon, Inc., Ramsey, NJ (US)

( * ) Notice: Subject to any disclaimer, the term of this patent is extended or adjusted under 35 U.S.C. 154(b) by 0 days.

(21) Appl. No.: 10/038,116

(22) Filed: Dec. 31, 2001

(65) Prior Publication Data

US 2002/0183317 A1 Dec. 5, 2002

Related U.S. Application Data

(60) Provisional application No. 60/296,247, filed on Jun. 6, 2001, provisional application No. 60/259,239, filed on Jan. 2, 2001, and provisional application No. 60/259,107, filed on Dec. 29, 2000.

(51) Int. Cl.$^7$ .............................................. A61K 31/425
(52) U.S. Cl. ....................................... 514/365; 514/367
(58) Field of Search ................................. 514/365, 367

(56) References Cited

U.S. PATENT DOCUMENTS

| | | | |
|---|---|---|---|
| 5,656,261 A | 8/1997 | Cerami et al. | 424/53 |
| 5,853,703 A * | 12/1998 | Cerami et al. | 424/53 |
| 6,007,865 A | 12/1999 | Cerami et al. | 424/656 |
| 6,440,749 B1 | 8/2002 | Cerami et al. | 436/815 |

FOREIGN PATENT DOCUMENTS

| | | |
|---|---|---|
| WO | WO 97/42175 | 11/1997 |
| WO | WO 01/62250 A1 | 2/2000 |
| WO | WO 02/08210 A1 | 7/2001 |

* cited by examiner

*Primary Examiner*—Raymond Henley, III
(74) *Attorney, Agent, or Firm*—Dechert

(57) ABSTRACT

Provided is a method of treating or ameliorating a number of indications in an animal, including a human, comprising administering an effective amount of a compound of the formula I or IA,

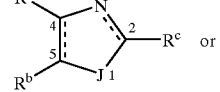

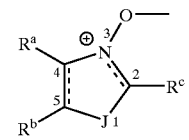

wherein J is oxygen, sulfur, or N—$R^d$.

16 Claims, No Drawings

METHOD FOR TREATING FIBROTIC DISEASES OR OTHER INDICATIONS IIC

The present application claims the priority of U.S. Applications 60/296,247, filed Jun. 6, 2001, No. 60/259,239, filed Jan. 2, 2001 and 60/259,107, filed Dec. 29, 2000.

The present invention relates to methods for treating certain fibrotic diseases or other indications, and to compounds and compositions for use in such treating.

Glucose and other sugars react with proteins by a non-enzymatic, post-translational modification process called non-enzymatic glycosylation. At least a portion of the resulting sugar-derived adducts, called advanced glycosylation end products (AGEs), mature to a molecular species that is very reactive, and can readily bind to amino groups on adjacent proteins, resulting in the formation of AGE cross-links between proteins. Recently a number of classes of compounds have been identified whose members inhibit the formation of the cross-links, or in some cases break the cross-links. These compounds include, for example, the thiazolium compounds described in U.S. Pat. No. 5,853,703. As AGEs, and particularly the resulting cross-links, are linked to several degradations in body function linked with diabetes or age, these compounds have been used, with success, in animal models for such indications. These indications include loss of elasticity in blood vasculature, loss of kidney function and retinopathy. Now, as part of studies on these compounds, it has been identified that these compounds inhibit the formation of bioactive agents, such as growth factors and inflammatory mediators, that are associated with a number of indications. These agents include vascular endothelial growth factor (VEGF) and TGF [beta]. As a result, a number of new indications have been identified for treatment with agents that inhibit the formation of, or more preferably break, AGE-mediated cross-links. It is not unreasonable to infer that the effects seen are due to the removal of AGE-related molecules that provide a stimulus for the production or release of these growth factors. Removal of such molecules is believed to proceed in part due to the elimination of AGE-related cross-links that lock the AGE-modified proteins in place. Moreover, such compounds also reduce the expression of collagen in conditions associated with excess collagen production. Regardless of the mechanism, now provided are new methods of treating a number of indications.

SUMMARY OF THE INVENTION

In one embodiment, the invention relates to a method of treating or ameliorating or preventing an indication of the invention in an animal, including a human, comprising administering an effective amount of a compound of the formula I or IA,

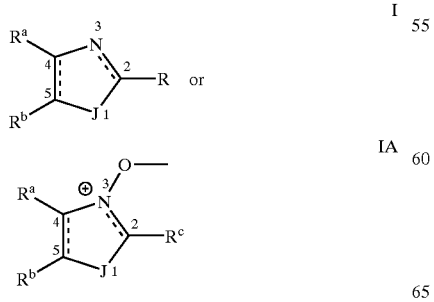

wherein the substituent groups are as defined below.

DETAILED DESCRIPTION OF THE INVENTION

The agents used in the invention are compounds or formulas I or IA, wherein:
a. J is oxygen, sulfur, or N—$R^d$;
b. the carbon 2 to nitrogen bond is a double bond except when $R^c$ is oxo;
c. the bond between carbons 4 and 5 is a single bond or a double bond (in one embodiment, a single bond);
d. $R^a$ and $R^b$ are
  1. independently selected from hydrogen, acylamino, acyloxyalkyl, alkanoyl, alkanoylalkyl, alkenyl, alkoxy, alkoxycarbonyl, alkoxycarbonylalkyl, alkyl, alkylamino, ($C_1$–$C_3$)alkylenedioxy, allyl, amino, ω-alkylenesulfonic acid, carbamoyl, carboxy, carboxyalkyl (which alkyl can be substituted with alkyloxyimino), cycloalkyl, dialkylamino, halo, hydroxy, ($C_2$–$C_6$)hydroxyalkyl, mercapto, nitro, sulfamoyl, sulfonic acid, alkylsulfonyl, alkylsulfinyl, alkylthio, trifluoromethyl, morpholin-4-yl, thiomorpholin-4-yl, piperidin-1-yl, 4-[$C_6$ or $C_{10}$]arylpiperidin-1-yl, 4-[$C_6$ or $C_{10}$]arylpiperazin-1-yl, Ar {wherein, consistent with the rules of aromaticity, Ar is $C_6$ or $C_{10}$ aryl or a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, each heteroaryl ring can be fused to a substituted benzene, pyridine, pyrimidine, pyrazine, pyridazine, or (1,2,3)triazine (wherein the ring fusion is at a carbon-carbon double bond of Ar) (or wherein Ar is as above but not heteroaryl fused to pyridine) (in one embodiment. Ar is $C_6$ or $C_{10}$ aryl)}, Ar-alkyl, ArO—, $ArSO_2$—, ArSO—, ArS—, $ArSO_2NH$—, ArNH, (N—Ar)(N-alkyl)N—, ArC(O)—, ArC(O)NH—, ArNH—C(O)—, and (N—Ar)(N-alkyl)N—C(O)—, or together $R^a$ and $R^b$ comprise methylenedioxy—(in one embodiment $R^a$ and $R^b$ are not acyloxyalkyl, alkenyl, ($C_1$–$C_3$) alkylenedioxy or allyl, or together do not comprise methylenedioxy); or
  2. together with their ring carbons form a $C_6$- or $C_{10}$-aryl fused ring; or
  3. together with their ring carbons form a $C_5$–$C_7$ fused cycloalkyl ring having up to two double bonds including any fused double bond of the containing group, which cycloalkyl ring can be substituted by one or more of the group consisting of alkyl, alkoxycarbonyl, amino, aminocarbonyl, carboxy, fluoro, or oxo (in one embodiment, the ring having no double bonds except any fused double bond of the formula I or IA ring, which cycloalkyl ring can be substituted by one or more of the group consisting of alkyl, amino, aminocarbonyl, carboxy, fluoro, or oxo, where multiple substituents are located on different carbon atoms of the cycloalkyl ring, except in the case of alkyl and fluoro substituents, which can be located on the same or different carbon atoms); or
  4. together with their ring carbons form a fused 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N; or
  5. together with their ring carbons form a fused five to eight membered second heterocycle (in one embodiment, a fused five to six membered second heterocycle), wherein the fused heterocycle consists of ring atoms selected from the group consisting of carbon, nitrogen, oxygen, sulfur, and $S(O)_n$, wherein n is 1 or 2;

e. $R^d$ is alkyl, alkenyl, hydrogen, or Ar;

f. $R^c$ is
  1. oxo (when $\Delta^{2,3}$ is not present), or (when $\Delta^{2,3}$ is present) hydrogen, alkyl, alkylthio, hydrogen, mercapto, amino, amino($C_1$–$C_5$)alkyl, or amino($C_6$ or $C_{10}$)aryl, or wherein the amino of the last three groups can be substituted with
    (a) Ar,
    (b) Ar—Z—, Ar-alkyl-Z—, Ar—Z-alkyl, Ar-amino-Z—, Ar-aminoalkyl-Z—, or Ar-oxyalkyl-Z—, wherein Z is a carbonyl or —$SO_2$—
    (c) formyl or alkanoyl (in one embodiment, $R^c$ is according to one of these optionally substituted three groups; in another, J is S or O (in one embodiment S), and $R^c$ is hydrogen, oxo, alkyl, amino, amino ($C_1$–$C_5$)alkyl or aminophenyl, wherein the amino of the latter three groups can be substituted as outlined here),
  2. —NHC(O)(CH$_2$)$_n$—D—$R^e R^f$ wherein D is oxygen, sulfur or nitrogen, wherein where D is nitrogen n is 0,1 or 2, but when D is oxygen or sulfur n=1 or 2, and $R^f$ is present only when D is nitrogen,
  wherein
    (a) $R^e$ is
      (1) Ar,
      (2) a group of the formula

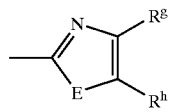

II wherein E is sulfur, oxygen, or N—$R^i$, and $R^g$, $R^h$ and $R^i$ are independently the same as $R^a$, $R^b$ and $R^d$, respectively,
      (3) a $C_3$–$C_8$ cycloalkyl ring having up to one double bond with the proviso that the carbon linking the cyloalkyl ring to D is saturated, which cycloalkyl ring can be substituted by one or more alkyl-, alkoxycarbonyl-, amino-, aminocarbonyl-, carboxy-, fluoro-, or oxo-substituents,
      (4) a 5- or 6-membered heteroaryl ring containing at least one and up to three atoms of N for the 6-membered heteroaryl rings and from one to three atoms of N or one atom of O or S and zero to two atoms of N for the 5-membered heteroaryl rings;
      (5) hydrogen, ($C_2$–$C_6$)hydroxyalkyl, alkanoylalkyl, alkyl, alkoxycarbonylalkyl, alkenyl, carboxyalkyl (which alkyl can be substituted with alkoxyimino), alkoxycarbonyl, a group $Ar^\phi$ which is $C_6$- or $C_{10}$-aryl or a 5- or 6-membered, or 9- or 10-membered heteroaryl (wherein the heteroatom is one oxygen, one sulfur or one nitrogen) or $Ar^\phi$-alkyl; and
    (b) $R^f$ is independently hydrogen, ($C_2$–$C_6$) hydroxyalkyl, alkanoylalkyl, alkyl, alkoxycarbonylalkyl, alkenyl, carboxyalkyl (which alkyl can be substituted with alkyloxyimino), alkoxycarbonyl, $Ar^\phi$, or $Ar^\phi$-alkyl;

wherein aryl, Ar, or $Ar^\phi$ can be substituted with, in addition to any substitutions specifically noted one or more general substituents selected from the group of acylamino, acyloxyalkyl, alkanoyl, alkanoylalkyl, alkenyl, alkoxy, alkoxycarbonyl, alkoxycarbonylalkyl, alkyl, alkylamino, ($C_1$–$C_3$)alkylenedioxy, alkylsulfonyl, alkylsulfinyl, ω-alkylenesulfonic acid, alkylthio, allyl, amino, ArC (O)—, ArC(O)NH—, carboxy, carboxyalkyl, cycloalkyl, dialkylamino, halo, trifluoromethyl, hydroxy, ($C_2$–$C_6$) hydroxyalkyl, mercapto, nitro, ArO—, Ar—, Ar-alkyl-, sulfamoyl, sulfonic acid, 1-pyrrolidinyl, 4-[$C_6$ or $C_{10}$] arylpiperazin-1-yl-, 4-[C6 or C10]arylpiperidin-1-yl, azetidin-1-yl, morpholin-4-yl, thiomorpholin-4-yl, piperidin-1-yl (in one embodiment, the substituents are selected from the group of aryl preferred general substituents which are: alkyl, amino, dialkylamino, 1-pyrrolidinyl, 4-[$C_6$ or $C_{10}$]arylpiperazin-1-yl, 4-[$C_6$ or $C_{10}$]arylpiperidin-1-yl, azetidin-1-yl, morpholin-4-yl, thiomorpholin-4-yl and piperidin-1-yl); and heterocycles, except those of Ar and $Ar^\phi$, can be substituted with in addition to any substitutions specifically noted one or more preferred substituents selected from acylamino, alkanoyl, alkoxy, alkoxycarbonyl, alkoxycarbonylalkyl, alkyl, ($C_1$ to $C_3$)alkylenedioxy, alkylamino, alkylsulfonyl, alkylsulfinyl, alkylthio, amino, ArC(O)—, ArO—, Ar—, Ar-alkyl, carboxy, dialkylamino, fluoro, fluoroalkyl, difluoroalkyl, hydroxy, mercapto, oxo, sulfamoyl, trifluoromethyl, 4-[$C_6$ or $C_{10}$]arylpiperidin-1-yl and 4-[$C_6$ or $C_{10}$]arylpiperazin-1-yl (in one embodiment, the substituents selected from heterocycle preferred general substituents: acylamino, alkanoyl, alkoxy, alkoxycarbonyl, alkoxycarbonylalkyl, alkyl, ($C_1$ to $C_3$)alkylenedioxy, alkylamino, alkylsulfonyl, alkylsulfinyl, alkylthio, amino, ArC(O)—, ArO—, Ar—, Ar-alkyl, carboxy, dialkylamino, fluoro, fluoroalkyl, difluoroalkyl, hydroxy, mercapto, oxo, sulfamoyl, trifluoromethyl, 4-[$C_6$ or $C_{10}$] arylpiperidin-1-yl and 4-[$C_6$ or $C_{10}$]arylpiperazin-1-yl, wherein multiple substituents are located on different atoms of the heterocyclic ring, with the proviso that alkyl, alkoxycarbonyl, and fluoro substituents can be substituted on the same carbon atom of the heterocyclic ring);

or a pharmaceutically acceptable salt of said compounds,
  with the proviso that where the compound of formula I is administered to decrease intraocular pressure at least one compound of formula I administered in effective amount is not a thiazole substituted on a ring carbon sulfonamide (the amide of which can be substituted) that has carbonic anhydrase inhibiting activity.

In addition to the methods, compounds, and compositions thereof described herein, the invention provides methods or use in the treatments of the invention, or in the manufacture of a medicament for such therapeutic use.

Certain Fibrotic Diseases

Among the indications that can be treated with the invention are a number of indications linked to or associated with the formation of excess collagen. Among these, a number of the indications can be termed fibrotic diseases.

Such fibrotic diseases include systemic sclerosis, mixed connective tissue disease, fibrodysplasia, fibrocystic disease, sarcoidosis, myositis (e.g. polymyositis, primary idiopathic polymyositis, childhood polymyositis, dermatomyositis, childhood dermatomyositis, primary idiopathic dermatomyositis in adults, inclusion body myositis, polymyositis or dermatomyositis associated with malignant tumors). Dermatomyositis can be associated with fibrosing or hypertrophic aspects, including fibrosing alveolitis and pulmonary fibrosis. Treatment using the invention is expected to treat, prevent, reduce or ameliorate such diseases or hypertrophy, fibrotic hypertrophy or fibrosis in such diseases. Amelioration includes reducing the rate of progression of a disease.

Among these fibrotic diseases are diseases that have as a manifestation fibrotic vascular intimal hypertrophy. These diseases include vasculitis (including coronary artery vasculitis), polyarteritis nodosa or temporal arteritis. Treatment using the invention is expected to treat, prevent, reduce or ameliorate vascular intimal hypertrophy in such diseases.

These fibrotic diseases further include diseases that have as a manifestation fibrotic hypertrophy of skin and/or muscle tissue. These diseases include scleroderma, eosinophilic fasciitis, discoid lesions associated with lupus or discoid lupus or surgical adhesions. Treatment using the invention is expected to treat, prevent, reduce or ameliorate such indications or hypertrophy or fibrosis of skin or muscle tissue.

Such fibrotic diseases further include diseases that have as a manifestation fibrotic hypertrophy of nerve tissue. These diseases include cerebrosclerosis, annular sclerosis. diffuse sclerosis and lobar sclerosis. Treatment using the invention is expected to treat, prevent, reduce or ameliorate such diseases, or hypertrophy, fibrotic hypertrophy or fibrosis of nerve tissue in such diseases.

These fibrotic diseases further include fibrotic lung diseases that have as a manifestation fibrotic hypertrophy or fibrosis of lung tissue. These diseases include pulmonary fibrosis (or interstitial lung disease or interstitial pulmonary fibrosis), idiopathic pulmonary fibrosis, the fibrotic element of pneumoconiosis (which is associated with exposure to environmental hazards such as smoking, asbestos, cotton lint, stone dust, mine dust and other particles), pulmonary sarcoidosis, fibrosing alveolitis, the fibrotic or hypertrophic element of cystic fibrosis, chronic obstructive pulmonary disease, adult respiratory distress syndrome and emphysema. Treatment using the invention is expected to treat, prevent, reduce or ameliorate such diseases, or hypertrophy, fibrotic hypertrophy or fibrosis in such diseases.

Such fibrotic diseases further include diseases that have as a manifestation fibrotic hypertrophy or fibrosis of prostate, liver, the pleura (e.g., pleurisy, pleural fibrosis) or pancreas. These diseases include benign prostatic hypertrophy (BPH) and fibrosis of the liver. Treatment using the invention is expected to treat, prevent, reduce or ameliorate such diseases, or hypertrophy, fibrotic hypertrophy or fibrosis in such diseases.

These fibrotic diseases further include diseases that have as a manifestation fibrotic hypertrophy or fibrosis of the bowel wall, such as inflammatory bowel disease, including Crohn's disease. Treatment using the invention is expected to treat, prevent, reduce or ameliorate such diseases, or hypertrophy, fibrotic hypertrophy or fibrosis in such diseases.

Arteriosclerosis, Atherosclerosis, Stiff Vessel Disease, Peripheral Vascular Disease, Coronary Heart Disease, Stroke, Myocardial Infarct, Cardiomyopathies, Restenosis Arteriosclerosis is a disease marked by thickening, hardening, and loss of elasticity in arterial walls, of which atherosclerosis is a sub-type. Arteriosclerosis in turn falls within the genus of stiff vessel diseases. Without limitation to theory, it is believed that damage to the blood vessels of these diseases is due to AGE-caused damage, either through protein cross-linking or the stimulation of bioactive agents, or both. Accordingly, the agents are used to treat, prevent, reduce or ameliorate stiff vessel disease, including arteriosclerosis and athersclerosis. Peripheral vascular disease is an indication that overlaps with atherosclerosis but also covers disease which is believed to have a stronger inflammatory component. First agents are used to treat, prevent, reduce or ameliorate peripheral vascular disease. Coronary heart disease is a form of atherosclerosis of the coronary arteries. First agents are used to treat, prevent, reduce or ameliorate coronary heart disease.

When the heart pumps blood into the vascular system, the ability of the arteries to expand helps to push blood through the body. When arteries become stiff, as they do in the natural process of aging, the ability of the arteries to expand is diminished and also has consequences for the heart. The heart has to work harder to pump the blood into the stiff arteries, and eventually hypertrophies (enlarges in size) to accomplish this. A hypertrophied heart is an inefficient pump, and is one of the disorders that leads to congestive heart failure. One compound believed to work by a mechanism shared by the compounds of the invention, 3-[2-phenyl-2-oxoethyl]-4,5-dimethyl-thiazolium salt, showed an ability to reverse the stiffness of arteries in a Phase IIa clinical trial, as measured by the ratio of stroke volume (ml) to pulse pressure (mm Hg). The potential clinical benefit of this is to lessen the effort that the heart must expend to push blood throughout the body. The effect is also believed to contribute to preventing hypertrophy and subsequent inefficiency of the heart, which inefficiency would contribute to congestive heart failure.

Stroke is a cardiovascular disease that occurs when blood vessels supplying blood (oxygen and nutrients) to the brain burst or are obstructed by a blood clot or other particle. Nerve cells in the affected area of the brain die within minutes of oxygen deprivation and loss of nerve cell function is followed by loss of corresponding bodily function. Of the four main types of stroke, two are caused by blood clots or other particles. The former two are the most common forms of stroke, accounting for about 70–80 percent of all strokes.

Blood clots usually form in arteries damaged by atherosclerosis. When plaque tears from the sheer forces of blood flowing over an uneven, rigid cap atop the plaque site, thrombotic processes become involved at the "injury" site. As a result, clots can form. First agents are used to prevent, reduce or ameliorate the risk of stroke in patients who have suffered previous strokes or have otherwise been identified as at risk.

First agents can also be used to treat, prevent, reduce or ameliorate peripheral vascular disease and periarticular rigidity.

Treatment with the agents during the relatively immediate aftermath of a heart attack can be used to reduce the size of the myocardial infarct resulting from the heart attack. This treatment is preferably administered within six hours of the heart attack, more preferably, within three hours. While the dosages discussed below can be used with this indication, such as a dose of 0.01–4.0 mg/kg administered orally or 0.01–2.0 mg/kg administered intravenously, preferably within the time period outlined above. Preferred routes of administration include i.v. injection or i.v. drip. Thereafter, optional supplemental administrations can be made with the dosages described below.

Atherosclerosis is a disease that involves deposition of blood lipids in plaque in the arteries throughout the body. In coronary arteries, accumulation of plaque progressively leads to reduced coronary flow, with occlusion of the arteries causing focal death of cardiac tissue (myocardial infarction, heart attack). If the amount of tissue that dies is large enough, death ensures. In a Phase IIa trial, one compound believed to work by a mechanism shared by the compounds of the invention, 3-[2-phenyl-2-oxoethyl]-4,5-dimethyl-thiazolium salt, increased the amount of circulating triglycerides (lipids). Consistent with the known presence of AGEs in plaque, the result indicates that the agent had a lipid mobilizing effect on arterial plaque. Reducing local deposits of plaque should eventually lessen the risk of myocardial infarction and death due to heart attacks.

Fibrotic diseases further include diseases that have as a manifestation fibrotic hypertrophy of the heart. These diseases include endomyocardial fibrosis (wherein endocardium and subendocardium are fibrosed, such as in some manifestations of restrictive cardiomyopathy), dilated congestive cardiomyopathy (a disorder of myocardial function with heart failure in which ventricular dilation and systolic dysfunction predominate), hypertrophic cardiomyopathy (characterized by marked ventricular hypertrophy with diastolic dysfunction in the absence of an afterload demand), and other cardio-hypertrophies. In dilated congestive cardiomyopathy, typically at presentation there is chronic myocardial fibrosis with diffuse loss of myocytes. In hypertrophic cardiomyopathy, usually the interventricular septum is hypertrophied more than the left ventricular posterior wall (asymmetric septal hypertrophy). Treatment using the invention is expected to treat, prevent, reduce or ameliorate such diseases, or hypertrophy, fibrotic hypertrophy or fibrosis in such diseases.

Hypertrophies of the heart can be diagnosed and monitored by methods known in the art, such as by electrocardiogram, echocardiography or magnetic resonance imaging. Such diagnostic methods can be applied in particular for subjects having a risk factor for such hypertrophy, such as congestive heart failure, prior cardiac surgery or diabetes. In one aspect, the invention comprises identifying cardio-hypertrophy with using biophysical diagnostic tools, and administering an active agent of the invention to treat, prevent, reduce or ameliorate such diseases, or hypertrophy, fibrotic hypertrophy or fibrosis in such diseases. The invention can further include monitoring cardio-hypertrophy during the course of treatment with active agent.

Erosion or tearing of arterial wall plaque can occur due to the rough and irregular shape of the plaque as it forms from deposition of lipids and invasion of cells such as monocytes and macrophages (foam cells). When erosion occurs platelets and other components of the blood clotting system are activated, resulting in formation of a clot (thrombus). When the thrombus grows to such as state that blood flow is reduced, severe angina attacks that characterize unstable angina can occur. Plaque forms irregular shapes and in doing so creates shear stresses from the flow of blood over this irregular form. It is the irregularity of plaque shape that leads to the dislodging or tearing of the plaque, and to the subsequent invasion of reactive cells. On the surface of plaque is collagen, which is believed to contribute to the rigidity of the irregular shape. Without limitation to theory, it is believed that reducing the crosslinking of such a rigid collagen cap results in smoother blood flow, with a reduced risk of angina-causing tears. Accordingly, agents are used to treat, prevent, reduce or ameliorate unstable angina.

Faithful conduction of the electrical impulse from the sinoatrial to the atrioventricular nodes depends upon close apposition of myocardial cells. Excess production of collagen in the heart, which occurs naturally with aging but more so in diabetes and in conditions of heart disorders such as hypertension, causes an increase in the distance between myocardial cells, leading to atrial fibrillation. First agents are used to treat, prevent, reduce or ameliorate atrial fibrillation.

The fibrotic indications further include restenosis, which is the process of increasing artery closure following an operation to open the artery, such as balloon angioplasty.

Bladder Elasticity

Indications that can be treated, prevented, reduced or ameliorated with the agents include loss of bladder elasticity. Bladder elasticity is tied to the frequency of urination, and the urgency of desire to urinate. Accordingly, the invention can be used to treat, prevent, reduce or ameliorate non-obstructive uropathy, a disorder characterized by an overactive bladder that entails increased frequency of urination, a strong and sudden desire to urinate (urgency) which may also be associated with involuntary urinary leakage (urge incontinence).

Macular Degeneration

The effect of the agents in reducing levels of other endogenous bioactive agents, particularly VEGF and/or TGF[beta], is believed to underlie effectiveness against macular degeneration. Again, however, the invention is not limited to theory.

Moreover, a anti-fibrotic effect or another effect against tissue hypertrophy may contribute. Treatment using the invention is expected to treat, prevent, reduce or ameliorate macular degeneration or macular edema. In one aspect of the invention, the treatment is used to treat, prevent, reduce or ameliorate the wet form of macular degeneration. In the wet form, new blood vessel growth has a greater contribution to the disease.

The composition used to in the method for macular degeneration includes an effective amount of an agent which is not a thiazole substituted on a ring carbon with sulfonamide (the amide of which can be substituted) that has carbonic anhydrase inhibiting activity. Of course, the composition can include an effective amount of an agent of the invention, as well as a carbonic anhydrase-inhibiting effective amount of another agent, including one of those distinguished above.

Amyotrophic Lateral Sclerosis (ALS)

ALS is associated with degradations of the motor neuron system and/or the posterior column of the spinal cord. In ALS patients, these structures tend to stain with AGE-reactive antibodies. Treatment using the invention is expected to treat, prevent, reduce or ameliorate ALS.

Rheumatoid Arthritis, Osteoarthritis, Bone Resorption

It is believed, without limitation to such theory, that reducing AGE accumulation at the joints affected by rheumatoid arthritis or osteoarthritis reduces stimulation of the production of cytokines involved in inflammatory processes of the disease. Treatment using the invention is expected to treat, prevent, reduce or ameliorate rheumatoid arthritis or osteoarthritis. Similarly, it is believed that reducing AGE accumulation at bone reduces stimulation of bone resorption. Accordingly, the invention is used to treat, prevent, reduce or ameliorate osteoporosis, bone loss or brittle bone.

Dialysis

The agents can be administered as part of a dialysis exchange fluid, thereby preventing, limiting or ameliorating the damage to tissue caused by the sugars found in such exchange fluid. For example, agents are expected to prevent, limit or ameliorate the stiffening and sclerosing of peritoneal tissue that occurs in peritoneal dialysis, as well as prevent, limit or ameliorate the formation of new blood vessels in the peritoneal membrane. In hemodialysis, agents are expected to prevent, limit or ameliorate the stiffening and sclerosing of red blood cells and vasculature resulting from exposure to the sugars exchanged into the blood during dialysis. Exchange fluids for peritoneal dialysis typically contain 10–45 g/L of reducing sugar, typically 25 g/L, which causes the formation of AGEs and consequent stiffening and degradation of peritoneal tissue. Similarly, hemodialysis fluids typically contain up to about 2.7 g/L of reducing sugar, typically 1 to 1.8 g/L. Thus, the invention provides methods by which the agents are provided in these fluids and thereby prevent, limit or ameliorate the damage that would otherwise result. Alternatively, the invention provides methods whereby the agents are administered by the methods described below to prevent, limit or ameliorate such damage from dialysis. In hemodialysis, the exchange fluid preferably contains 0.006–2.3 mg/L of an agent of the invention, more preferably, 0.06 to 1.0 mg/L. In peritoneal dialysis, the exchange fluid preferably contains 0.01 to 24 mg/L of an agent of the invention, or preferably, 1.0 to 10 mg/L.

In one embodiment, preventing or ameliorating is effected with a second agent. A preferred route of administration is inclusion in the dialysis fluids. In hemodialysis, the exchange fluid preferably contains 0.125 to 2.5 mg/L of aminoguanidine, more preferably, 0.2 to 1.0 mg/L. In peritoneal dialysis, the exchange fluid preferably contains 1.25 to 25 mg/L of aminoguanidine, or preferably, 2.0 to 10 mg/L. In a preferred aspect of the invention, the agents are initially administered, and subsequently second agents are used to moderate or limit damage thereafter.

Asthma

It is believed, without limitation to such theory, that the agents or second agents act to prevent, reduce or ameliorate the small but significant thickening of the lung airways associated with asthma. Moreover, the agents are believed to reduce stimulation of the production of cytokines involved in inflammatory processes of the disease. Accordingly, the agents are used to treat, prevent, reduce or ameliorate asthma. In this embodiment, one preferred route of administration is pulmonary, such as via an aerosol, though peroral administration is also preferred.

Carpal Tunnel Syndrome

It is believed, without limitation to such theory, that the agents act to prevent, reduce or ameliorate fibrotic and cytokine-induced elements of carpal tunnel syndrome. Accordingly, the agents are used to treat, prevent, reduce or ameliorate carpal tunnel syndrome.

Fibrotic diseases also include Dupuytren's contracture, a contracture of the palmar fascia often causing the ring and little fingers to bend into the palm. Treatment using the invention is expected to treat, prevent, reduce or ameliorate Dupuytren's contracture, or hypertrophy, fibrotic hypertrophy or fibrosis in Dupuytren's contracture.

In these embodiments, one preferred route of administration is local injection.

Periodontal Disease

The incidence of periodontal disease is higher in subjects with either insulin-deficient or insulin-resistant diabetes, with consequent hyperglycemia. Again, without limitation to such theory, it is believed that the agents act to prevent, reduce or ameliorate AGE-induced cytokine action to create or exacerbate periodontal disease. Accordingly, the first or second agents are used to treat, prevent, reduce or ameliorate periodontal disease. In this embodiment, one preferred primary or supplemental route of administration is via mouthwash, or compositions adapted for delivery into the subgingival periodontal pocket (such as implants and erodible microspheres). Peroral administration is again useful. The mouthwash preferably contains 0.003–1.0 mg/L of a agent, more preferably, 0.01–0.1 mg/L.

Sickle Cell Anemia

It is believed, without limitation to such theory, that the agents act to prevent, reduce or ameliorate the restraint on blood flow caused by sickling. Again without limitation to theory, the mode of action is believed to be in reducing vascular as well as blood cell inelasticity. Accordingly, the agents are used to treat, prevent, reduce or ameliorate a sickle cell anemia.

Erectile Dysfunction

Fibrotic diseases further include diseases that have as a manifestation fibrotic disease of the penis, including Peyronie's disease (fibrosis of the cavernous sheaths leading to contracture of the investing fascia of the corpora, resulting in a deviated and painful erection). Treatment using the invention is expected to treat, prevent, reduce or ameliorate such diseases, or hypertrophy, fibrotic hypertrophy or fibrosis in such diseases.

Without limitation to theory, it is believed that the agents act to prevent, reduce or ameliorate inelasticity of tissue of the penis and/or fibrosis of tissue of the penis, such as inelasticity or fibrosis of the cavernous sheaths leading to contracture of the investing fascia of the corpora. At least partial restoration of the resulting inelasticity is believed to facilitate engorgement of the corpora cavernosa with blood. Accordingly, the agents are used to treat, prevent, reduce or ameliorate erectile dysfunction.

Limited Joint Mobility

Limited Joint Mobility (LJM) is a disorder associated with diabetes and typically involves the joints of the hands. The fourth and fifth fingers are affected initially by limitation of motion. AGE glycation and crosslinking of tendons (collagen) in the joints is believed to contribute to the disease. It is believed, without limitation to theory, that the agents act to prevent, reduce or ameliorate inelasticity, fibrous tissue or cytokine-induced inflammation associated with limited joint mobility. Accordingly, the agents are used to treat, prevent, reduce or ameliorate limited joint mobility.

Antineoplastic Applications

The agents inhibit the stimulated formation of bioactive agents, such as VEGF, associated with angiogenesis. Angiogenesis is critical for both normal development and the growth and metastasis of solid tumors. Accordingly, the agents are used to treat, prevent, reduce or ameliorate the growth of neoplasms by limiting the formation of blood vessels needed to sustain the neoplasms.

End Stage Renal Disease, Diabetic Nephropathy

Diabetic Nephropathy is a complication of diabetes that evolves early, typically before clinical diagnosis of diabetes is made. The earliest clinical evidence of nephropathy is the appearance of low but abnormal levels (>30 mg/day or 20 μg/min) of albumin in the urine (microalbuminuria), followed by albuminuria (>300 mg/24 h or ~200 μg/min) that develops over a period of 10–15 years, in patients with type 1 diabetes, diabetic hypertension typically becomes manifest early on, by the time that patients develop microalbuminuria. Once overt nephropathy occurs, the glomerular filtration rate (GFR) falls over several years resulting in End Stage Renal Disease (ESRD) in 50% of type 1 diabetic individuals within 10 years and in >75% of type 1 diabetics by 20 years of onset of overt nephropathy. Albuminuria (i.e., proteinuria) is a marker of greatly increased cardiovascular morbidity and mortality for patients with either type 1 or type 2 diabetes.

Without limitation to theory, it is believed that damage to the glomeruli and blood vessels of the kidney is due to AGE-caused damage, either through protein cross-linking or the stimulation of bioactive agents, or both. Accordingly, the agents are used to treat, prevent, reduce or ameliorate damage to kidney in patients at risk for ESRD. The agents can also be used to treat, prevent, reduce or ameliorate glomerulosclerosis.

Hypertension, Isolated Systolic Hypertension

Cardiovascular risk correlates more closely with the systolic and the pulse pressure than with the diastolic pressure. In diabetic patients, the cardiovascular risk profile of diabetic patients is strongly correlated to duration of diabetes, glycemic control and blood pressure. Structural matrix proteins contribute to the function of vessels and the heart, and changes in the physical behavior of cardiovascular walls are believed to be important determinants of circulatory function. In elderly individuals, the loss of compliance in the aorta leads to isolated systolic hypertension, which in turn expands the arterial wall and thereby diminishes the dynamic range of elasticity. In vivo studies in rodents, canines and in primates indicate potential utility of 3-[2-phenyl-2-oxoethyl]-4,5-dimethyl-thiazolium salt in substantially ameliorating vascular stiffening. For example, in a dog model for diabetes, lower end diastolic pressure and increased end diastolic volume, indicators of ventricular elasticity, returned to a value at about the mid-point between the disease impaired value and the value for control dogs. Treatment with 3-[2-phenyl-2-oxoethyl]-4,5-dimethyl-thiazolium salt lead to a reduction in the mass of collagen in cardiovascular tissues. In situ hybridization studies demonstrate that 3-[2-phenyl-2-oxoethyl]-4,5-dimethyl-thiazolium salt reduces the expression of both Type IV collagen and TGFbeta.

Compared with that of a non-diabetic, the diabetic artery is smaller as it is stiffer. As in isolated systolic hypertension in which vessels stiffen with age and lose the dynamic range of expansion under systole. First agents are used to treat, prevent, reduce or ameliorate hypertension, including isolated systolic hypertension and diabetic hypertension. Moreover, the same benefit is anticipated for the more rare hypertensive disorder, pulmonary hypertension. Pulmonary hypertension is a rare blood vessel disorder of the lung in which the pressure in the pulmonary artery (the blood vessel that leads from the heart to the lungs) rises above normal levels and may become life threatening. The similarity in development of elevated blood pressure in the pulmonary bed with the increase in systemic blood pressure in diabetic hypertension and in isolated systolic hypertension suggests similar mechanisms are involved.

Pulse pressure is the difference between systolic and diastolic blood pressure. In a young human, systolic pressure is typically 120 mm Hg and diastolic pressure is 80 mm Hg, resulting in a pulse pressure of 40 mm Hg. With age, in many individuals pulse pressure increases, largely due to the increase in systolic pressure that results from stiff vessel disease. In individuals with pulse pressure greater than 60 mm Hg there is an increased risk of death from cardiovascular morbidities. In a Phase Ia trial, one compound believed to work by a mechanism shared by the compounds of the invention, 3-[2-phenyl-2-oxoethyl]-4,5-dimethyl-thiazolium salt, reduced pulse pressure in elderly patients with pulse pressures greater than 60 mm Hg in a statistically significant manner. This decrease in pulse pressure was believed to be due primarily to the effect of the agent on lowering the systolic blood pressure.

The agents of the invention are used to treat, prevent, reduce or ameliorate reduced vascular compliance, elevated pulse pressure, and hypertension. Moreover, the agents are used to reduce pulse pressure, increase vascular compliance, or decrease the risk of death.

Heart Failure

Congestive Heart Failure (CHF) is a clinical syndrome that entails cardiac disease of the ventricle. Diastolic dysfunction is a subset of heart failure in which the left ventricle stiffens with age. The stiffening of the left ventricle that occurs in CHF and in diastolic dysfunction is believed to result from increased crosslinking of collagen fibers with age and/or fibrosis and related hypertrophy. First agents are used to treat, prevent, reduce or ameliorate heart failure.

Retinopathy

The effect of diabetes on the eye is called diabetic retinopathy and involves changes to the circulatory system of the retina. The earliest phase of the disease is known as background diabetic retinopathy wherein the arteries in the retina become weakened and leak, forming small, dot-like hemorrhages. These leaking vessels often lead to swelling or edema in the retina and decreased vision. The next stage is proliferative diabetic retinopathy, in which circulation problems cause areas of the retina to become oxygen-deprived or ischemic. New vessels develop as the circulatory system attempts to maintain adequate oxygen levels within the retina. Unfortunately, these new vessels hemorrhage easily. In the later phases of the disease, continued abnormal vessel growth and scar tissue may cause serious problems such as retinal detachment and glaucoma. First agents are used to treat, prevent, reduce or ameliorate diabetic retinopathy. The agents can be administered by the methods described below, including by topical administration to the eye. The agents can also be administered by intravitreal implant.

Cataracts, Other Damage to Lens Proteins

AGE-mediated crosslinking and/or fibrotic processes are believed to contribute to cataract formation and formation of other damage to lens proteins. First agents are used to treat, prevent, reduce or ameliorate cataracts or other damage to lens proteins.

Alzheimer's Disease

Considerable evidence exists implicating AGEs that form in the neurofibrillary tangles (tau protein) and senile plaques (beta-amyloid peptide) in early neurotoxic processes of Alzheimer's disease. Insoluble human tau protein is likely crosslinked. Glycation of insoluble tau from AD patients and experimentally AGE-modified tau generate oxygen free radicals, resulting in the activation of transcription via nuclear factor-kappa B, and resulting in an increase in amyloid beta-protein precursor and release of amyloid beta-peptides. Thus, A.G.E.-modified tau may function as an initiator in a positive feedback loop involving oxidative stress and cytokine gene expression. First agents are used to treat, prevent, reduce or ameliorate Alzheimer's disease.

Other indications

For reasons analogous to those set forth above, the invention is believed to be useful in treating, preventing, reducing or ameliorating diabetes or its associated adverse sequelae, and peripheral neuropathy. The agents, especially in topical form, increase elasticity and/or reduce wrinkles in skin. The agents further increase red blood cell deformability.

Combination Therapies

In cardiovascular therapies, agents can be administered concurrently or in a combined formulation with one or more antioxidants. Examples of appropriate antioxidants are vitamin A, vitamin B6, vitamin C, vitamin E, glutathione, β-carotene, α-lipoic acid, coenzyme Q10, selenium and zinc, which are administered in effective amounts as is known in the art. Thus, the invention further provides pharmaceutical compositions comprising an agent of the invention in combination with an effective amount of an antioxidant.

In treating heart failure, cardiomyopathy or heart attack, agents can be administered concurrently or in a combined formulation with one or more angiotensin converting enzyme (ACE) inhibitors, angiotensin II receptor antagonists, calcuim channel blockers, diuretics, digitalis or beta blockers. Examples of ACE inhibitors include Captopril, Enalapril, Enalaprilat, Quinapril, Lisinopril and Ramipril, which are administered in effective amounts as is known in the art. Examples of angiotensin II receptor antagonists include Losartan, Irbesartan, Eprosartan, Valsartan and Candesartan, which are administered in effective amounts as is known in the art. Examples of calcium channel blockers include Amlopdipine, Bepridil, Diltiazem, Felodipine, Isradipine, Nicardipine, Nifedipine, Nimodipine and Verapamil, which are administered in effective amounts as is known in the art. Among diuretics, preferred examples include Furosemide, Bumetanide, Torsemide, Ethacrynic acid, Azosemide, Muzolimine, Piretanide, Tripamide and Hydrochlorothiazide, which are administered in effective amounts as is known in the art. Examples of beta adrenergic antagonists include Metoprolol, Carvedilol, Bucindolol, Atenolol, Esmolol, Acebutolol, Propranolol, Nadolol, Timolol, Pindolol, Labetalol, Bopindolol, Carteolol, Penbutolol, Medroxalol, Levobunolol, Bisoprolol, Nebivolol, Celiprolol and Sotalol, which are administered in effective amounts as is known in the art. Thus, the invention further provides pharmaceutical compositions comprising an agent of the invention in combination with an effective amount of an ACE inhibitor, diuretic, digitalis, beta blocker, or combination thereof.

For treating diabetes or complications thereof, the invention further provides pharmaceutical compositions comprising an agent of the invention in combination with an effective amount of a thiazolidinedione or "glitazone" diabetes drug, such as Troglitazone, Rosiglitazone, and Pioglitazone.

In treating atherosclerosis, agents can be administered concurrently or in a combined formulation with one or more statins (HMG CoA reductase inhibitors) or cholestyramine. Examples of statins include Mevastatin, Lovastatin, Simvastatin, Pravastatin and Fluvastatin, which are administered in effective amounts as is known in the art. Thus, the invention further provides pharmaceutical compositions comprising an agent of the invention in combination with an effective amount of a statin, cholestyramine, or both.

For a number of indications discussed, including sickle cell enemia and diabetic complications, as well as wound healing and any other indication in which increased tissue perfusion is a useful means or adjunct to therapy, the agents, or aminoguanidine or other agents of the aminoguanidine class can be administered with erythropoietin, which is administered in effective amount as is known in the art. Erythropoietin includes stable forms of erythropoietin such as are marketed by Amgen (Thousand Oaks, Calif.).

For all indications, agents can be administered concurrently or in a combined formulation with aminoguanidine or other agents of the aminoguanidine class, which are administered in effective amounts as is known in the art. These agents include compounds of formula A

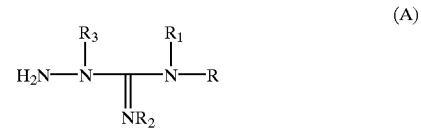

(A)

wherein R is an alkyl group, or a group of the formula —N($R^4$)($R^5$) wherein $R^4$ is hydrogen, and $R^5$ is an alkyl group or a hydroxyalkyl group; or $R^4$ and $R^5$ together with the nitrogen atom are a heterocyclic group containing 4–6 carbon atoms and, in addition to the nitrogen atom, 0–1 oxygen, nitrogen or sulfur atoms; $R^1$ is hydrogen or an amino group; $R^2$ is hydrogen or an amino group; $R^3$ is hydrogen or an alkyl group, wherein R and $R^1$ cannot both be amino groups. Preferably at least one of $R^1$, $R^2$, and $R^3$ is other than hydrogen. The compounds can be used as their pharmaceutically acceptable acid addition salts, and mixtures of such compounds. When aminoguanidine compounds are administered, they can be administered by any route of pharmaceutical administration including those discussed below for other first agents.

The method of the invention is used to treat animals, preferably mammals, preferably humans.

In accordance with the present invention, methods for administering pharmaceutical compositions containing compounds have been developed for the treating the indications of the invention. These agents are either substituted thiazole, oxazole, or imidazole agents as shown in the Summary section above.

As is noted in the formula for I and IA, the invention includes aromatic thiazole, oxazole, and imidazole analogs, as well as non aromatic analogs thereof such as thiazoline, thiazolidine, oxazoline, oxazolidine, imidazoline, and imidazolidine analogs.

The alkyl, and alkenyl groups referred to above include both C1 to C6 linear and branched alkyl and alkenyl groups, unless otherwise noted. Alkoxy groups include linear or branched C1 to C6 alkoxy groups, unless otherwise noted.

"Ar" (consistent with the rules governing aromaticity) refers to a $C_6$ or $C_{10}$ aryl, or a 5 or 6 membered heteroaryl ring. The heteroaryl ring contains at least one and up to three atoms of N for the 6 membered heteroaryl ring. The 5 membered heteroaryl ring contains; (1) from one to three atoms of N, or (2) one atom of O or S and zero to two atoms of N. Nonlimiting examples of heteroaryl groups include: pyrrolyl, furanyl, thienyl, pyridyl, oxazolyl, pyrazolyl, pyrimidinyl, and pyridazinyl.

"Ar" can be fused to either a benzene, pyridine, pyrimidine, pyridazine, or (1,2,3) triazine ring.

As used herein, $C_6$ or $C_{10}$ aryl groups and heteroaryl containing five or six, or nine to ten ring members are monocyclic or bicyclic.

In certain embodiments of the invention, the thiazoles, imidazoles, and oxazoles of the invention contain $R^a$ and $R^b$ substitutions that together with their ring carbons (the C4–C5 carbons of the thiazoles, imidazoles, and oxazoles) form a five to eight membered fused heterocycle (i.e. a bicyclic heterocycle is formed). In these embodiments the fused heterocycle is preferably not aromatic. Particular compounds within these embodiments contain sulfur atoms in the fused heterocycle (the ring fused to the thiazoles, imidazoles, and oxazoles). These sulfur atoms in these particular compounds can exist in various oxidation states, as $S(O)_n$, where n is 0, 1, or 2.

In certain embodiments of the invention, thiazoles, imidazoles, and oxazoles of the invention contain $R^a$ and $R^b$ substitutions that together with their ring carbons (the C4–C5 carbons of the thiazoles, imidazoles, and oxazoles) form a C5 to C7 cycloalkyl ring having up to double bonds including the C4–C5 double bond. In other embodiments a cycloalkyl ring is present when $R^e$ is a C3 to C8 cycloalkyl ring. The cycloalkyl groups can be substituted by one or more of the group consisting of alkyl-, alkoxycarbonyl-, amino-, aminocarbonyl-, carboxy-, fluoro-, or oxo-substituents. One of ordinary skill in the art will recognize that where cycloalkyl groups contain double bonds, the $sp^2$ hybridized carbon atoms can contain only one substituent (which cannot be amino- or oxo-). $Sp^3$ hybridized carbon atoms in the cycloalkyl ring can be geminally substituted with the exception that (1) two amino groups and (2) one amino and one fluoro group can not be substituted on the same $sp^3$ hybridized carbon atom.

In certain embodiments of the invention, the thiazoles, imidazoles, and oxazoles of the invention contain $R^a$ and $R^b$ substitutions that together with their ring carbons (the C4–C5 carbons of the thiazoles, imidazoles, and oxazoles) form a five or six membered heteroaryl ring (i.e., a bicyclic aromatic heterocycle is formed). A preferred bicyclic aromatic heterocycle of the invention is a purine analog [J is N—$R^d$ and $R^a$ and $R^b$ together with their ring carbons (the C4 and C5 of the imidazole ring) form a pyrimidine ring].

Aryl, Ar, or $Ar^\Phi$ can be substituted with, in addition to any substitutions specifically noted one or more substituents selected from the group of acylamino, acyloxyalkyl, alkanoyl, alkanoylalkyl, alkenyl, alkoxy, alkoxycarbonyl, alkoxycarbonylalkyl, alkyl, alkylamino, (C1–C3) alkylenedioxy, alkylsulfonyl [alkylSO$_2$—], alkylsulfinyl [alkylSO—], ω-alkylenesulfonic acid [—(CH$_2$)$_n$SO$_3$H where n=1 to 6], alkylthio, allyl, amino, ArC(O)—, ArC(O)NH—, carboxy, carboxyalkyl, cycloalkyl, dialkylamino, halo, trifluoromethyl, hydroxy, (C2–C6)hydroxyalkyl, mercapto, nitro, ArO—, Ar—, Ar-alkyl-, sulfamoyl, sulfonic acid, morpholin-4-yl, thiomorpholin-4-yl, piperidin-1-yl, 1-pyrrolidinyl, 4-[C$_6$ or C$_{10}$]arylpiperidin-1-yl and 4-[C$_6$ or C$_{10}$]arylpiperazin-1-yl.

Heterocycles, except those of Ar and $Ar^\Phi$, can be substituted with in addition to any substitutions specifically noted one or more substituents selected from acylamino, alkanoyl, alkoxy, alkoxycarbonyl, alkoxycarbonylalkyl, alkyl, (C1 to C3)alkylenedioxy, alkylamino, alkylsulfonyl, alkylsulfinyl, alkylthio, amino, ArC(O)—, ArO—, Ar—, Ar-alkyl, carboxy, dialkylamino, fluoro, fluoroalkyl, difluoroalkyl, hydroxy, mercapto, oxo, sulfamoyl, trifluoromethyl, 4-[C$_6$ or C$_{10}$]arylpiperidin-1-yl and 4-[C$_6$ or C$_{10}$]arylpiperazin-1-yl, wherein multiple substituents are located on different atoms of the heterocyclic ring, with the proviso that alkyl, alkoxycarbonyl, and fluoro substituents can be substituted on the same carbon atom of the heterocyclic ring. Heterocycles can be substituted with one or more substituents.

The halo atoms can be fluoro, chloro, bromo or iodo. Chloro and fluoro are preferred for aryl substitutions.

In some embodiments of this invention, the compounds of formula (I) can form biologically and pharmaceutically acceptable salts. Useful salt forms include the halides (particularly bromides and chlorides), tosylates, methanesulfonates, brosylates, fumarates, maleates, succinates, acetates, mesitylenesulfonates, and the like. Other related salts can be formed using similarly non-toxic, biologically or pharmaceutically acceptable anions.

Representative, non-limiting examples of compounds of the present invention are:

Thiazole 4,5-Dimethylthiazole

4-Methylthiazole

5-Methylthiazole

4-Methyl-5-(2-hydroxyethyl)thiazole

4-Methyl-5-vinylthiazole

Benzothiazole

2-Aminobenzothiazole

2-Amino-4-chlorobenzothiazole

2-Amino-6-chlorobenzothiazole 2,6-Diamino-benzothiazole

2-Aminothiazole 2,4,5-Trimethylthiazole

2-Amino-5-methylthiazole

2-Amino-4-methylthiazole

2-Acetylthiazole

2-Ethyl-4-methylthiazole

Ethyl 2-(Formylamino)-4-thiazoleacetate 2-(Formylamino)-alpha-(methoxyimino)-4-thiazoleacetic acid 2-Amino-4-phenylthiazole hydrochloride monohydrate 2-Isobutylthiazole 2-Methyl-2-thiazoline 2-Methyl-2-oxazoline 2-Oxazolidone 2-Amino-4-thiazoleacetic acid 1-(Thiazolyl)-3-phenyl-urea 1-(Thiazolidinyl)-3-(4-fluorophenyl)-urea (4-fluorophenyl)thiazolin-2-ylamine 2-(4,6-dimethylpyrimidin-2-ylthio)-N-(1,3-thiazol-2'yl) acetamide, also known as N-(Thiazolyl)-2-(4,6-dimethyl-pyrimidin-2-yl-thio)-acetamide

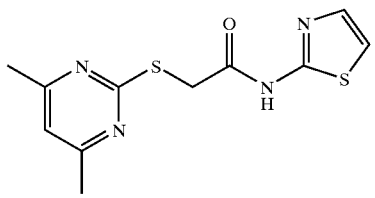

2-(4-propylphenoxy)-N-(thiazol-2-yl)acetamide 2-furyl-N-[4-(6-methylbenzothiazol-2-yl)phenyl]carboxamide 2-(3,5-Dimethylphenoxy)-N-thiazol-2-yl)acetamide 5,5-Dimethyl-2-(2-naphthylamino)-4,5,6-trihydrobenzothiazol-7-one Imidazole 1-Methylimidazole 1-Ethylimidazole 1-Butylimidazole 1-Vinylimidazole 1-Allylimidazole 1-(Trimethylsilyl) imidazole 1-(3-Aminopropyl) imidazole 1-Benzyl imidazole 1-Phenyl imidazole 1,5-Dicyclohexyl imidazole 1-(p-Toluenesulfonyl) imidazole N-Benzoyl-imidazole 4-Methyl-imidazole 4'-(Imidazol-1-yl)-acetophenone 4-(Imidazol-1-yl)-phenol 1-(4-Methoxyphenyl)-1H-imidazole Methyl-4-(1H-imidazol-1yl)benzoate 1-Methylbenzimidazole as well as other biologically and pharmaceutically acceptable salts thereof.

Where one or more compounds of formula I are administered to decrease intraocular pressure, at least one compound of formula I administered in effective amount is not a thiazole substituted on a ring carbon sulfonamide (the amide of which can be substituted) that has carbonic anhydrase inhibiting activity. Of course, the composition can include an effective amount of a agent, as well as a carbonic anhydrase-inhibiting effective amount of another agent, including one of those distinguished above.

Compounds of the formula I can be conveniently prepared by chemical syntheses well-known in the art. Certain of the compounds are well-known and readily available from chemical supply houses or can be prepared by synthetic methods specifically published therefor. For instance, 4,5-Dimethylthiazole, 4-Methylthiazole, 5-Methylthiazole, 4-Methyl-5-thiazoleethanol, 4-Methyl-5-vinylthiazole, Benzothiazole, 2-Aminobenzothiazole, 2-Amino-4-chlorobenzothiazole, 2-Amino-6-chlorobenzothiazole, 2-Aminothiazole, 2,4,5-Trimethylthiazole, 2-Amino-5-methylthiazole, 2-Amino-4-methylthiazole, 2-Acetylthiazole, 2-Ethyl-4-methylthiazole, Ethyl 2-(Formylamino)-4-thiazoleacetate, 2-(Formylamino)-alpha-(methoxyimino)-4-thiazoleacetic acid, 2-amino-4-phenylthiazole hydrochloride monohydrate, 2-Isobutylthiazole, 2-Methyl-2-thiazoline, 2-Methyl-2-oxazoline, 2-Oxazolidone, Thiomorpholine, 2-Amino-4-thiazoleacetic acid, Imidazole, 1-Methylimidazole, 1-Butylimidazole, 1-Vinylimidazole, 1-Allylimidazole, 1-(Trimethylsilyl) imidazole, 1-(3-Aminopropyl) imidazole, 1-Benzyl imidazole, 1-Phenyl imidazole, 1,5-Dicyclohexyl imidazole, 1-(p-Toluenesulfonyl) imidazole, N-Benzoyl-imidazole, 4-Methyl-imidazole, 4'-(Imidazol-1-yl)-acetophenone, 4-(Imidazol-1-yl)-phenol, 1-(4-Methoxyphenyl)-1H-imidazol and 1-Methylbenzimidazole can be obtained from Sigma (St. Louis, Mo.), Aldrich (Milwakee, Wis.) or Fluka (Milwaukee, Wis.) (all divisions of Sigma-Aldrich Co.). 1-ethylimidazole can be obtained from TCI America (Portland, Oreg.). N-(Thiazolidinyl)-4-fluoroaniline, N-(Thiazolyl)-2-(4,6-dimethyl-pyrimidin-2-yl-thio)-acetamide, N-(Thiazolyl)-2-(4-propylphenoxy)-acetamide, 2-[4-(N-Furoyl)aminophenyl]-6-methylbenzothiazole, N-(Thiazolyl)-2-(3,5-dimethylphenoxy'-acetamide and 2-[(N-(2-Napthalenyl)amino]-[2,3:5,4]-(5,5-dimethyl-cyclohexanonyl)]thiazole can be purchased from MDD, Inc. (Acton, Ontario), a successor to Ortech Corporation.

In one synthetic process to prepare compounds of the general formula I, a thiazole is reacted with an alkyl or acyl halide in the presence of base such as triethylamine, to produce the corresponding alkyl or acyl derivative at the 2 carbon. See, Medici et al.,*J. Org. Chem.* 49: 590–596, 1984. In some cases, a chromatographic step is applied to separate additions at the 2 and 3 positions of the thiazole ring.

In another synthesis of compounds of the formula I wherein $R^c$ is amino, nitro-containing analogs of compounds of the invention or precursors thereof are catalytically hydrogenated to the corresponding amino compounds. 2-Amino thiazole compounds wherein ($R^c$ is amino) can also be synthesized by reacting thiourea (which can be substituted on at least one amine) with an alpha-halo ketone using the method described in *Vogel's Textbook of practical Organic Chemistry*, 5th Edition, John Wiley & Sons, New York, p. 1153. Such a reaction is exemplified by a synthesis of 2-amino-4-phenylthiazole:

Scheme 1

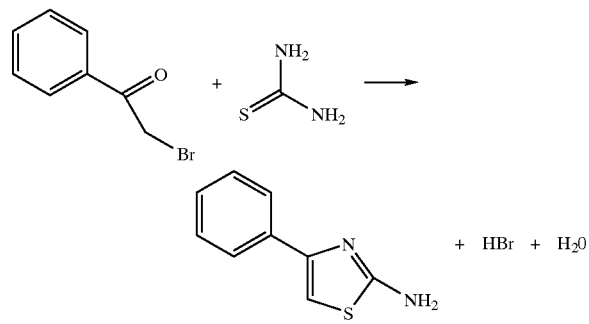

N-aryl imidazoles can be prepared using appropriate aromatic nucleophilic displacement reactions. For example, fluoro phenyl compounds such as 4-fluorobenzoic acid methyl ester can be used to substitute the $N^1$ nitrogen of imidazole to make methyl-4-(1H-imidazol-1-yl)benzoate. See, Morgan et al., *J. Med. Chem.* 33: 1091–1097, 1990.

Amino functions of 2-aminoimidazoles or 2-aminothiazoles can be acylated by dehydration or other methods known in the art.

Substituted oxazoles can be prepared by methods known in the art. For instance, 2-unsubstituted oxazoles can be formed by condensation of formamide with either α-hydroxy or α-haloketones intermediates (H. Bredereck, R. Gommper, H. G. v. Shuh and G. Theilig, in Newer Methods of Preparative Organic Chemistry, Vol. III, ed. W. Foerst, Academic press, New York, 1964, p. 241). The intermediates can cyclize under acid conditions to form the oxazole ring (Scheme 2). In addition, 2,4-disubstituted oxazoles can be prepared from α-haloketones and amides at higher temperatures using the same method.

Scheme 2

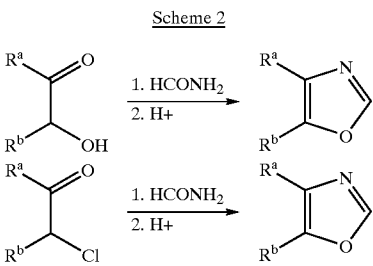

Oxazoles can be prepared by cyclization reactions of isonitriles (van Leusen, A. M. *Lect. Heterocycl. Chem.* 1980, 5, S111; Walborsky, H. M.; Periasamy, M. P. in *The Chemistry of Functional Groups, suppl.* C, Patai, S.; Rappoport, Z., Eds; Wiley-Interscience, 1983, p. 835; Hoppe, D. *Angew. Chem. Int. Edn. Engl.,* 1974, 13, 789; Schollkopf, U. *Angew. Chem. Int. Ed. Engl.,* 1977, 16, 339). For example, as shown below in Scheme 3, the tosylmethyl isocyanide can be deprotonated by a base and reacted with a suitable electrophile (e.g. an aldehyde). The intermediate can cyclize and aromatize to provide the desired oxazole analog. Other methods for preparing oxazoles include 1,5-dipolar cyclization of acylated nitrile ylides (Taylor E. C.; Turchi, I. J. *Chem. Rev.,* 1979, 79, 181; Huisgen, R. *Angew. Chem. Int. Edn. Engl.* 1980, 19, 947)

Scheme 3

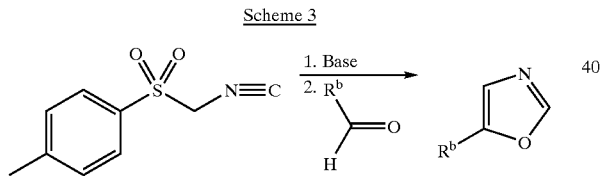

2-Amino-substituted oxazoles (i.e. $R^c$=NH$_2$) can be prepared by two general methods. Urea can be condensed with α-bromo ketones to yield 2-aminooxazoles that can be substituted at the 4 and 5 positions (Scheme 4). Alternatively, another route to 2-aminooxazoles from acyclic precursors is the base catalyzed reaction of cyanamide with α-hydroxy ketones (Scheme 5). 2-Aminooxazoles of the invention can also be prepared from the nucleophilic displacement of amines with 2-chlorooxazole, for example, for compounds of the invention wherein $R^c$ is ArNH— (Gompper, R.; Effenberger, F. *Chem. Ber.,* 1959, 92, 1928).

Scheme 4

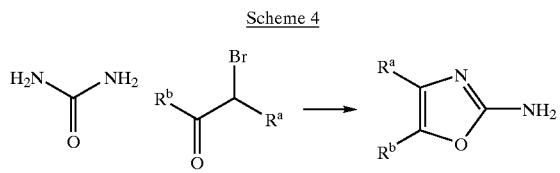

Scheme 5

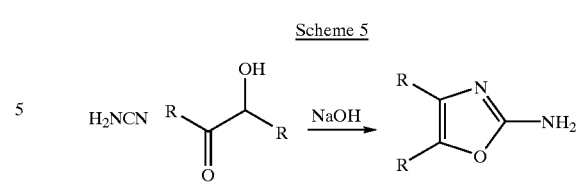

Compounds of the invention, wherein $R^c$ is arylcarbonyl can be synthesized by acylation of the amino moiety of 2-aminooxazoles with, for example, with anhydrides to yield 2-acylaminooxazoles. In addition, 2-aminooxazoles can be acylated, for instance, with chloroacetic anhydride to yield an α-chloro carboxamide. The α-chloro carboxamide can serve as a suitable alkylating reagent that can be treated with, for example, phenols, arylamines and alkylamines to prepare compounds of the invention. An oxazole of the invention wherein Rc is Ar-oxycarbonylamino is shown in Scheme 6.

Scheme 6

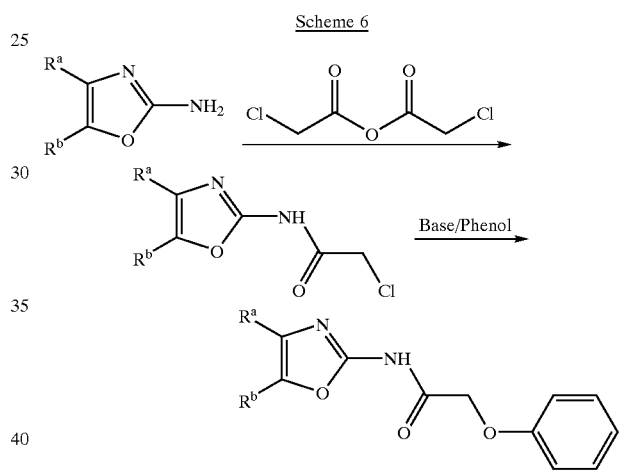

Oxazoles of the invention with Rc is aminocarbonylamino (ureido) or aminothiocarbonylamino (thioureido) can be prepared from 2-aminooxazoles (Scheme 7). 2-Aminooxazoles can be treated with isocyanates and isothiocyanates to yield 2-ureido and 2-thioureido oxazoles, respectively (Crank, G.; Foulis, J. *J. Med. Chem.,* 1971, 14, 1075: Crank, G. Neville, M.; Ryden, R. *J. Med Chem.,* 1974, 16, 1402).

Scheme 7

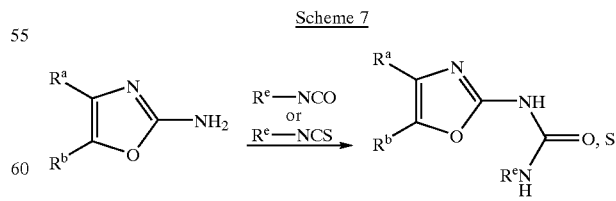

2-Aminooxazoles can be hydrogenated using palladium catalysts to yield 2-aminooxazolines (Scheme 8) (Tanaka, C.; Kuriyama, S. *Yakugaku Zasshi* 1979, 99, 78).

Scheme 8

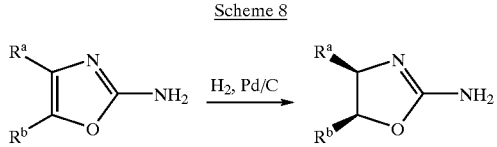

Benzoxazole intermediates substituted at the 2 position can be prepared from 2-aminophenols by acylation with, for example, with an acid chloride and cyclization (Scheme 9).

Scheme 9

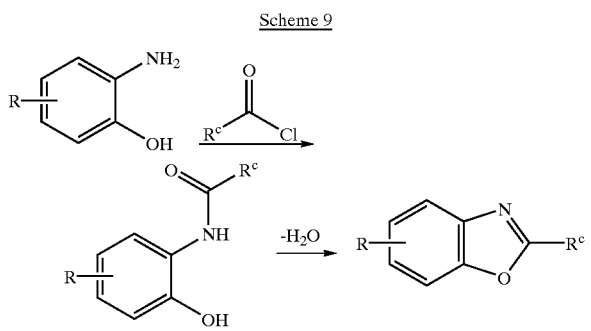

To treat the indications of the invention, an effective amount of a pharmaceutical compound will be recognized by clinicians but includes an amount effective to treat, reduce, ameliorate, eliminate or prevent one or more symptoms of the disease sought to be treated or the condition sought to be avoided or treated, or to otherwise produce a clinically recognizable change in the pathology of the disease or condition.

Pharmaceutical compositions can be prepared to allow a therapeutically effective quantity of the compound of the present invention, and can include a pharmaceutically acceptable carrier, selected from known materials utilized for this purpose. See, e.g., Remington, The Science and Practice of Pharmacy, 1995; Handbook of Pharmaceutical Excipients, $3^{rd}$ Edition, 1999. Such compositions can be prepared in a variety of forms, depending on the method of administration.

In addition to the subject compound, the compositions of this invention can contain a pharmaceutically-acceptable carrier. The term "pharmaceutically-acceptable carrier", as used herein, means one or more compatible solid or liquid filler diluents or encapsulating substances that are suitable for administration to an animal, including a mammal or human. The term "compatible", as used herein, means that the components of the composition are capable of being commingled with the subject compound, and with each other, such that there is no interaction that would substantially reduce the pharmaceutical efficacy of the composition under ordinary use. Preferably when liquid dose forms are used, the compounds of the invention are soluble in the components of the composition. Pharmaceutically-acceptable carriers must, of course, be of sufficiently high purity and sufficiently low toxicity to render them suitable for administration to the animal being treated.

Some examples of substances which can serve as pharmaceutically-acceptable carriers or components thereof are sugars, such as lactose, glucose and sucrose; starches, such as corn starch and-potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the subject compound is basically determined by the way the compound is to be administered. If the subject compound is to be injected, the preferred pharmaceutically-acceptable carrier is sterile, physiological saline, with a blood-compatible suspending agent, the pH of which has been adjusted to about 7.4.

If the preferred mode of administering the subject compound is perorally, the preferred unit dosage form is therefore tablets, capsules, lozenges, chewable tablets, and the like. Such unit dosage forms comprise a safe and effective amount of the subject compound, which is preferably from about 0.7 or 3.5 mg to about 280 mg/70 kg, more preferably from about 0.5 or 10 mg to about 210 mg/70 kg. The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder-mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of this invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.012% to about 0.933% of the subject compound, more preferably from about 0.033% to about 0.7%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Compositions can also be used to deliver the compound to the site where activity is desired; such as eye drops, gels and creams for ocular disorders.

Compositions of this invention include solutions or emulsions, preferably aqueous solutions or emulsions comprising a safe and effective amount of a subject compound intended for topical intranasal administration. Such compositions preferably comprise from about 0.01% to about 10.0% w/v of a subject compound, more preferably from about 0.1% to about 2.0%. Similar compositions are preferred for systemic delivery of subject compounds by the intranasal route. Compositions intended to deliver the compound systemically by intranasal dosing preferably comprise similar amounts of a subject compound as are determined to be safe and effective by peroral or parenteral administration. Such compositions used for intranasal dosing also typically include safe and effective amounts of preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acids and bases to adjust the pH of these aqueous compositions as needed. The compositions may also comprise local anesthetics or other actives. These compositions can be used as sprays, mists, drops, and the like.

Other preferred compositions of this invention include aqueous solutions, suspensions, and dry powders comprising a safe and effective amount of a subject compound intended for atomization and inhalation administration. Such compositions are typically contained in a container with attached atomizing means. Such compositions also typically include propellants such as chlorofluorocarbons 12/11 and 12/114, and more environmentally friendly fluorocarbons, or other nontoxic volatiles; solvents such as water, glycerol and ethanol, these include cosolvents as needed to solvate or suspend the active; stabilizers such as ascorbic acid, sodium metabisulfite; preservatives such as cetylpyridinium chloride and benzalkonium chloride; tonicity adjustors such as sodium chloride; buffers; and flavoring agents such as sodium saccharin. Such compositions are useful for treating respiratory disorders, such as asthma and the like.

Other preferred compositions of this invention include aqueous solutions comprising a safe and effective amount of a subject compound intended for topical intraocular administration. Such compositions preferably comprise from about 0.01% to about 0.8% w/v of a subject compound, more preferably from about 0.05% to about 0.3%. Such compositions also typically include one or more of preservatives, such as benzalkonium chloride or thimerosal; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases can be used to adjust the pH of these formulations as needed.

Other preferred compositions of this invention useful for peroral administration include solids, such as tablets and capsules, and liquids, such as solutions, suspensions and emulsions (preferably in soft gelatin capsules), comprising a safe and effective amount of a subject compound. Such compositions can be coated by conventional methods, typically with pH or time-dependent coatings, such that the subject compound is released in the gastrointestinal tract at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit™ coatings, waxes and shellac.

The compounds of the invention are administered by ocular, oral, parenteral, including, for example, using formulations suitable as eye drops. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchromium chloride, and the usual quantities of diluents and/or carriers. See, Remington's Pharmaceutical Sciences, 16th Ed., Mack Publishing, Easton, Pa., 1980, as well as later editions, for information on pharmaceutical compounding.

Numerous additional administration vehicles will be apparent to those of ordinary skill in the art, including without limitation slow release formulations, liposomal formulations and polymeric matrices.

In another preferred embodiment, the pharmaceutically effective amount is approximately 0.1 or 0.5 to 4 mg/kg body weight daily. Still more preferably, the pharmaceutically effective amount is approximately 1 mg/kg body weight daily. In a preferred embodiment, the amount is administered in once daily doses, each dose being approximately 1 mg/kg body weight.

The activity of the compounds of the invention in breaking, reversing or inhibiting the formation of AGE's or AGE-mediated cross-links can be assayed by any of the methods described in U.S. Pat. No. 5,853,703.

The following examples further illustrate the present invention, but of course, should not be construed as in any way limiting its scope.

EXAMPLE

Rats received a daily intraperitoneal dose of 10 mg/kg 3-[2-phenyl-2-oxoethyl]-4,5-dimethyl-thiazolium salt (compound A) (n=14) or placebo (n=15) for 30 days. The animals then underwent a thoracotomy and the left anterior descending coronary artery ligated. The chest was then closed and the animals allowed to recover for 14 days while continuing to be treated with compound A or placebo. The animals were then sacrificed and the hearts removed for histological examination. The weight of the infarcted tissue was 0.16±0.04 g for the placebo treated animals compared to 0.11±0.05 g for the compound A treated animals (p=0.04). The thickness of the ventricular wall in the infarcted zone was also reduced in the compound A treated animals compared to placebo (2.72±0.13 mm vs. 2.56±0.22 mm, p=0.09).

Example 1

2,6-diamino-benzothiazole dihydrochloride: 4 g of 2-amino-6-nitrobenzothiazole (Aldrich) was suspended in 130 ml MeOH, and 0.4 g 10% Pd/c (Aldrich) added. The suspension was hydrogenated at room temperature under 60 psi $H_2$ for 6.5 h. The reaction mixture was filtered, and the particulate washed with MeOH. The filtrate was concentrated under reduced pressure, and crystals formed from the concentrate were collected to yield 2.67 g. mp 196–198° C., yield 81.6%. 0.91 g of this product was dissolved in 22 ml MeOH, and the pH adjusted with HCl to 4 to produce 1.2 g of crystals of 2,6-diamino-benzothiazole dihydrochloride.

mp 318–320° C., 92.3% yield. Anal. calc. for $C_7H_9N_3SCl_2$, C 35.30%, H 3.80%, N 17.64%. Found, C 34.91%, H 3.67%, N 17.71%.

Example 2

2-(3,5-Dimethylphenoxy)-N-thiazol-2-yl)acetamide: First Route: 3,5-Dimethylphenol is reacted with bromoacetic acid at 110° C. for four hours, with the reaction mixture stirred overnight without added heat. The resulting (3,5-dimethylphenoxy)acetic acid is dissolved in methylene chloride and coupled to 2-aminothiazole in an overnight, room temperature reaction conducted in the presence of base (N-methylmorpholine) and dehydration mediators 1-hydroxybenzotriazole and 1-(3-dimethylaminopropyl)-3-ethyl-carbodiimide hydrochloride.

Second Route: 3,5-Dimethylphenol is reacted for 4.5 h with bromoacetic acid in THF under nitrogen and in the presence of sodium hydride. The resulting (3,5-dimethylphenoxy)acetic acid is reacted overnight with thionyl chloride, with heat. The resulting (3,5-dimethylphenoxy) acetyl chloride is reacted overnight with 2-aminothiazole in the presence of triethylamine, with cooling to 0C.

Third Route: 2-Aminothiazole (20 g, 199.7 mmol) was suspended in methylene chloride (200 ml), in the presence of pyridine (20 ml, ~250 mmol), and the mixture cooled to 0° C. Bromoacetyl bromide (18.1 ml, 207.6 mmol) was dissolved in 400 ml methylene chloride, and this solution added to the suspended 2-aminothiazole dropwise. The resulting reaction mixture was stirred at room temperature overnight. The crude product was washed with water (200 ml, 1x), then sodium bicarbonate solution (200 ml, 2x), dried over $Na_2SO_4$, filtered, and evaporated. The product 2-bromoacetamidothiazole was crystallized from MeOH. Yield, 4 g. mp 148° C.

A solution of 3,5-dimethylphenol (2.5 g, 13.9 mmol) in dry DMF (20 ml) was placed under a dry nitrogen atmosphere. Sodium hydride (0.7 g, 27.8 mmol; a 60% dispersion in mineral oil) was added in portions, and the mixture stirred for 1 h. A solution of 2-bromoacetamidothiazole (3.0 g, 13.9 mmol) in dry DMF (10 ml) was added to the mixture dropwise. The reaction was heated to 90° C. for 5 h, then maintained overnight without external heat. The reaction mixture was poured into ice water, and the resulting material extracted with methylene chloride (50 ml×3). The organic layer was washed with water (100 ml×5), dried over $Na_2SO_4$, filtered, and evaporated. The residue from evaporation was purified by silica gel chromatography developed with pet. ether:ether (1:1 v/v). The product N-(Thiazolyl)-2-(3,5-dimethylphenoxy)-acetamide was crystallized from acetonitrile and methyl tert-butyl ether. Yield, 1.04 g. mp 124–125° C.

Example 3

2-Furyl-N-[4-(6-methyl-benzothiazol-2-yl)phenyl] carboxamide: First Route: 2-Furoic acid (1.85 gms, 16.5 mmole) was dissolved in anhydrous methylene chloride (30 mls), to which solution was added a suspension of 2-(4-amino-phenyl)-6-methyl benzothiazole (4.76 g., 16.5 mmole) and N-methyl morpholine (2.0 g., 16.5 mmole) in methylene chloride (30 mls, at room temperature). Then, 1-hydroxy-benzotriazole hydrate (2.67 g., 16.5 mmole) and 1-(3-dimethyl amino propyl)-3-ethyl carbodiimide hydrochloride (4.75 g., 16.5 mmole) were added at room temperature. More methylene chloride (20 ml.) was added with stirring at room temperature, and the reaction maintained overnight. The initial clear reaction solution changed to a turbid solution. More methylene chloride (10 ml.) was added to the product mixture, which was then extracted with 1N HCl to separate a solid. The solid was filtered and washed with water. The product solid was crystallized from large amount of MeOH to yield 2.19 gm. (33.1%). mp. 238–240° C. $^1H$ and $^{13}C$ NMR were consistent with the expected product. TLC showed one spot (5% MeOH—$CH_2Cl_2$ as developing solvent on silica gel plate).

Route 2: 2-(4-aminophenyl)-6-methyl benzothiazole (2.0 gm, 8.3 mmole) and 2-Furoyl chloride (1.086 gm., 8.32 mmole) were suspended in methylene chloride (30 ml, anhydrous). triethylamine (1.24 gm., 12.25 mmole) was added to the reaction mixture with stirring at room temperature for 2 days. (pH 7.0–7.2). Methylene chloride (50 ml) was added to the reaction mixture, and the reaction mixture extracted with 1 N HCl (50 ml) to separate a solid. The solid was filtered and washed with water to yield 1.3 gm. (46%) of the desired compound. The product was crystallized from MeOH to obtain 0.99 gm. mp. 238–240° C. $^1H$ and $^{13}C$ NMR were consistent with the expected product. TLC showed one spot (5% MeOH—$CH_2Cl_2$ as developing solvent on silica gel plate).

Example 4

Cross-Linking Inhibition Assay

The following method was used to evaluate the ability of the compounds to inhibit the cross-linking of glycated bovine serum albumin (AGE-BSA) to rat tail tendon collagen-coated 96-well plates.

AGE-BSA was prepared by incubating BSA at a concentration of 200 mg per ml with 200 mM glucose in 0.4M sodium phosphate buffer, pH 7.4 at 37° C. for 12 weeks. The glycated BSA was then extensively dialyzed against phosphate buffer solution (PBS) for 48 hours with additional 5 times buffer exchanges. The rat tail tendon collagen coated plate was blocked first with 300 microliters of Superbloc blocking buffer (Pierce Chemical, Rockford, Ill.) for one hour. The blocking solution was removed from the wells by washing the plate twice with phosphate buffered saline (PBS)-Tween 20 solution (0.05% Tween 20) using a NUNC-multiprobe (Nalge Nunc, Rochester, N.Y.) or Dynatech ELISA-plate (Dynatech, Alexandria, Va.) washer. Cross-linking of AGE-BSA (1 to 10 microgram per well depending on the batch of AGE-BSA) to rat tail tendon collagen coated plate was performed with and without the testing compound dissolved in PBS buffer at pH 7.4 at one or more desired concentrations by the addition of 50 microliters each of the AGE-BSA diluted in PBS or in the solution of test compound at 37° C. for 4 hours. Unbrowned BSA in PBS buffer with or without testing compound were added to the separate wells as the blanks. The un-cross-linked AGE-BSA was then removed by washing the wells three times with PBS-Tween buffer. The amount of AGE-BSA crosslinked to the tail tendon collagen-coated plate was then quantitated using a polyclonal antibody raised against AGE-RNase. After a one-hour incubation period, AGE antibody was removed by washing 4 times with PBS-Tween.

The bound AGE antibody was then detected with the addition of horseradish peroxidase-conjugated secondary antibody—goat anti-rabbit immunoglobulin and incubation for 30 minutes. The substrate of 2,2-azino-di(3-ethylbenzthiazoline sulfonic acid) (ABTS chromogen) (Zymed Laboratories, Inc., South San Francisco, Calif.) was added. The reaction was allowed for an additional 15 minutes and the absorbance was read at 410 nm in a Dynatech plate reader.

Example 5

Cross-Link Breaking Assay

To ascertain the ability of the compounds of the instant invention to break or reverse already formed advanced glycosylation endproducts, a sandwich enzyme immunoassay was applied. Generally, the assay utilizes collagen-coated 96 well microtiter plates that are obtained commercially. AGE-modified protein (AGE-BSA) is incubated on the collagen-coated wells for four hours, is washed off the wells with PBS-Tween and solutions of the test compounds are added. Following an incubation period of 16 hours (37° C.) cross-link-breaking is detected using an antibody raised against AGE-ribonuclease or with an antibody against BSA.

Preparation of Solutions and Buffers

Bovine Serum Albumin (Type V) (BSA) (from Calbiochem) solution was prepared as follows: 400 mg of Type V BSA (bovine serum albumin) was added for each ml of 0.4 M sodium phosphate buffer, pH 7.4. A 400 mM glucose solution was prepared by dissolving 7.2 grams of dextrose in 100 ml of 0.4 M sodium phosphate buffer, pH 7.4. The BSA and glucose solutions were mixed 1:1 and incubated at 37° C. for 12 weeks. The pH of the incubation mixture was monitored weekly and adjusted to pH 7.4 if necessary. After 12 weeks, the AGE-BSA solution was dialyzed against PBS for 48 hours with four buffer changes, each at a 1:500 ratio of solution to dialysis buffer. Protein concentration was determined by the micro-Lowry method. The AGE-BSA stock solution was aliquoted and stored at −20° C.

Test compounds were dissolved in PBS and the pH was adjusted to pH 7.4, if necessary. AGE-BSA stock solution was diluted in PBS to measure maximum crosslinking and in the inhibitor solution for testing inhibitory activity of compounds. The concentration of AGE-BSA necessary to achieve the optimum sensitivity was determined by initial titration of each lot of AGE-BSA.

Substrates for detection of secondary antibody binding were prepared by diluting the HRP substrate buffer (Zymed) 1:10 in distilled water and mixing with ABTS chromogen (Zymed) 1:50 just prior to use.

Assay Procedures

Biocoat plates were blocked with 300 microliters of Superbloc (Pierce Chemical). Plates were blocked for one hour at room temperature and were washed with PBS-Tween (0.05% v/v) three times with the Dynatech platewasher before addition of test reagents.

The first three wells of the Biocoat plate were used for the reagent blank. Fifty microliters of solutions AGE-BSA were added to test wells in triplicate and only PBS in blank wells. The plate was incubated at 37° C. for four hours and washed with PBS-Tween three times. Fifty microliters of PBS was added to the control wells and 50 microliters of the test prospective agent was added to the test wells and blank. The plate was incubated overnight (approximately 16 hours) with prospective agent, followed by washing in PBS before addition of primary antibody.

(Prior to use, each lot of primary antibody, either anti-BSA or anti-RNase, was tested for optimum binding capacity in this assay by preparing serial dilutions (1:500 to 1:2000) and plating 50 microliters of each dilution in the wells of Biocoat plates. Optimum primary antibody was determined from saturation kinetics.) Fifty microliters of primary antibody of appropriate dilution, was added and incubated for one hour at room temperature. The plate was then washed with PBS-Tween.

Plates were incubated with the secondary antibody, HRP-(Goat-anti-rabbit), which was diluted 1:4000 in PBS and used as the final secondary antibody. The incubation was performed at room temperature for thirty minutes.

Detection of maximum crosslinking and breaking of AGE crosslinking was performed as follows. HRP substrate (100 microliter) was added to each well of the plate and was incubated at 37° C. for fifteen minutes. Readings were taken in the Dynatech ELISA-plate reader.

DEFINITIONS

Heterocycle. Except where heteroaryl is separately recited for the same substituent, the term "heterocycle" includes heteroaryl.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of treating or ameliorating certain fibrotic diseases, arteriosclerosis, atherosclerosis, stiff vessel disease, peripheral vascular disease, coronary heart disease, stroke, myocardial infarct, cardiomyopathies, restenosis, loss of bladder elasticity, macular degeneration, amyotrophic lateral sclerosis (ALS), rheumatoid arthritis, osteoarthritis, osteorporeosis, tissue damage caused by dialysis, asthma, carpal tunnel syndrome, periodontal disease, sickle cell anemia, erectile dysfunction, limited joint mobility, growth of neoplasms, end stage renal disease, diabetic nephropathy, hypertension, isolated systolic hypertension, heart failure, retinopathy, cataracts, other damage to lens proteins, Alzheimer's disease, diabetes or its associated adverse sequelae, peripheral neuropathy, or wrinkles in skin in an animal comprising administering an effective amount of a compound of the formula I or IA,

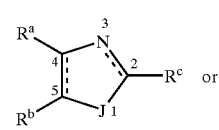

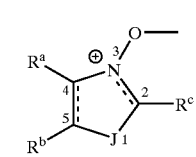

wherein:
a. J is oxygen, sulfur, or N—$R^d$;
b. the carbon 2 to nitrogen bond is a double bond except when $R^c$ is oxo;
c. the bond between carbons 4 and 5 is a single bond or a double bond;
d. $R^a$ and $R^b$ are
  1. independently selected from hydrogen, acylamino, acyloxyalkyl, alkanoyl, alkanoylalkyl, alkenyl, alkoxy, alkoxycarbonyl, alkoxycarbonylalkyl, alkyl, alkylamino, ($C_1$–$C_3$)alkylenedioxy, allyl, amino, ω-alkylenesulfonic acid, carbamoyl, carboxy, carboxyalkyl (which alkyl can be substituted with alkyloxyimino), cycloalkyl, dialkylamino, halo, hydroxy, ($C_2$–$C_6$)hydroxyalkyl, mercapto, nitro, sulfamoyl, sulfonic acid, alkylsulfonyl, alkylsulfinyl, alkylthio, trifluoromethyl, morpholin-4-yl, thiomorpholin-4-yl, piperidin-1-yl, 4-[$C_6$ or $C_{10}$]arylpiperidin-1-yl, 4-[$C_6$ or $C_{10}$]arylpiperazin-1-yl, Ar {wherein, consistent with the rules of aromaticity, Ar is $C_6$ or $C_{10}$ aryl or a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, each heteroaryl ring can be fused to a substituted benzene, pyridine, pyrimidine, pyrazine, pyridazine, or (1,2,3)triazine (wherein the ring fusion is at a carbon-carbon double bond of Ar)}, Ar-alkyl, ArO—, $ArSO_2$—, ArSO—, ArS—, $ArSO_2NH$—, ArNH, (N—Ar)(N-alkyl)N—, ArC(O)—, ArC(O)NH—, ArNH—C(O)—, and (N—Ar)(N-alkyl)N—C(O)—, or together $R^a$ and $R^b$ comprise methylenedioxy-; or
  2. together with their ring carbons form a $C_6$- or $C_{10}$-aryl fused ring; or
  3. together with their ring carbons form a $C_5$–$C_7$ fused cycloalkyl ring having up to two double bonds including any fused double bond of the containing group, which cycloalkyl ring can be substituted by one or more of the group consisting of alkyl, alkoxycarbonyl, amino, aminocarbonyl, carboxy, fluoro, or oxo; or
  4. together with their ring carbons form a fused 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N; or
  5. together with their ring carbons form a fused five to eight membered second heterocycle, wherein the fused heterocycle consists of ring atoms selected from the group consisting of carbon, nitrogen, oxygen, sulfur, and $S(O)_n$, wherein n is 1 or 2;
b. $R^d$ is alkyl, alkenyl, hydrogen, or Ar;
c. $R^c$ is
  1. oxo (when $\Delta^{2,3}$ is not present), or (when $\Delta^{2,3}$ is present) hydrogen, alkyl, alkylthio, hydrogen, mercapto, amino, amino($C_1$–$C_5$)alkyl, or amino($C_6$ or $C_{10}$)aryl, or wherein the amino of the last three groups can be substituted with
    (a) Ar,
    (b) Ar—Z—, Ar-alkyl-Z—, Ar—Z-alkyl, Ar-amino-Z—, Ar-aminoalkyl-Z—, or Ar-oxyalkyl-Z—, wherein Z is a carbonyl or —$SO_2$—
    (c) formyl or alkanoyl, 2. —$NHC(O)(CH_2)_n$—D—$R^eR^f$, wherein D is oxygen, sulfur or nitrogen, wherein where D is nitrogen n is 0, 1 or 2, but when D is oxygen or sulfur n=1 or 2, and $R^f$ is present only when D is nitrogen, wherein
    (a) $R^e$ is
      (1) Ar,
      (2) a group of the formula

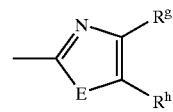

II wherein E is sulfur, oxygen, or N—$R^i$, and $R^g$, $R^h$ and $R^i$ are independently the same as $R^a$, $R^b$ and $R^d$, respectively,
      (3) a $C_3$–$C_8$ cycloalkyl ring having up to one double bond with the proviso that the carbon linking the cyloalkyl ring to D is saturated, which cycloalkyl ring can be substituted by one or more alkyl-, alkoxycarbonyl-, amino-, aminocarbonyl-, carboxy-, fluoro-, or oxo-substituents;
      (4) a 5- or 6-membered heteroaryl ring containing at least one and up to three atoms of N for the 6-membered heteroaryl rings and from one to three atoms of N or one atom of O or S and zero to two atoms of N for the 5-membered heteroaryl rings;
      (5) hydrogen, (C2–C6)hydroxyalkyl, alkanoylalkyl, alkyl, alkoxycarbonylalkyl, alkenyl, carboxyalkyl (which alkyl can be substituted with alkoxyimino), alkoxycarbonyl, a group $Ar^\phi$ which is $C_6$- or $C_{10}$-aryl or a 5- or 6-membered, or 9- or 10-membered heteroaryl (wherein the heteroatom is one oxygen, one sulfur or one nitrogen) or $Ar^\phi$-alkyl; and
    (b) $R^f$ is independently hydrogen, (C2–C6) hydroxyalkyl, alkanoylalkyl, alkyl, alkoxycarbonylalkyl, alkenyl, carboxyalkyl (which alkyl can be substituted with alkyloxyimino), alkoxycarbonyl, $Ar^\phi$, or $Ar^\phi$-alkyl;
wherein aryl, Ar, or $Ar^\phi$ can be substituted with, in addition to any substitutions specifically noted one or more substituents selected from the group of acylamino, acyloxyalkyl, alkanoyl, alkanoylalkyl, alkenyl, alkoxy, alkoxycarbonyl, alkoxycarbonylalkyl, alkyl, alkylamino, ($C_1$–$C_3$)alkylenedioxy, alkylsulfonyl, alkylsulfinyl, ω-alkylenesulfonic acid, alkylthio, allyl, amino, ArC(O)—, ArC(O)NH—, carboxy, carboxyalkyl, cycloalkyl, dialkylamino, halo, trifluoromethyl, hydroxy, ($C_2$–$C_6$) hydroxyalkyl, mercapto, nitro, ArO—, Ar—, Ar-alkyl-, sulfamoyl, sulfonic acid, 1-pyrrolidinyl, 4-[$C_6$ or $C_{10}$] arylpiperazin-1-yl-, 4-[C6 or C10]arylpiperidin-1-yl, azetidin-1-yl, morpholin-4-yl, thiomorpholin-4-yl, piperidin-1-yl; and
heterocycles, except those of Ar and $Ar^\phi$, can be substituted with in addition to any substitutions specifically noted one or more substituents selected from acylamino, alkanoyl, alkoxy, alkoxycarbonyl, alkoxycarbonylalkyl, alkyl, (C1 to C3)alkylenedioxy, alkylamino, alkylsulfonyl, alkylsulfinyl, alkylthio, amino, ArC(O)—, ArO—, Ar—, Ar-alkyl, carboxy, dialkylamino, fluoro, fluoroalkyl, difluoroalkyl, hydroxy, mercapto, oxo, sulfamoyl, trifluoromethyl, 4-[$C_6$ or $C_{10}$]arylpiperidin-1-yl and 4-[$C_6$ or $C_{10}$]arylpiperazin-1-yl;
or a pharmaceutically acceptable salt of said compounds.

2. The method of claim 1, comprising administering an effective amount of a compound of the formula I, wherein the bond between carbons 4 and 5 is a single bond.

3. The method of claim 1, comprising administering an effective amount of a compound of the formula I, wherein $R^c$ is amino, amino($C_1$–$C_5$)alkyl, or amino($C_6$ or $C_{10}$)aryl, or wherein the amino of any of the three groups can be substituted with
   (a) Ar;
   (b) Ar—Z—, Ar-alkyl-Z—, Ar—Z-alkyl, Ar-amino-Z—, Ar-aminoalkyl-Z—, or Ar-oxyalkyl-Z—, wherein Z is a carbonyl or —$SO_2$—; or
   (c) formyl or alkanoyl.

4. The method of claim 1, comprising administering an effective amount of a compound of the formula I, wherein J is S or O, and $R^c$ is hydrogen, oxo, alkyl, amino, amino($C_1$–$C_5$)alkyl or aminophenyl, wherein the amino of the latter three groups can be substituted with
   (a) Ar;
   (b) Ar—Z—, Ar-alkyl-Z—, Ar—Z-alkyl, Ar-amino-Z—, Ar-aminoalkyl-Z—, or Ar-oxyalkyl-Z—, wherein Z is a carbonyl or —$SO_2$—; or
   (c) formyl or alkanoyl.

5. The method of claim 1, comprising administering an effective amount of a compound of the formula I, wherein J is S, and $R^c$ is hydrogen, oxo, alkyl, amino, amino($C_1$–$C_5$) alkyl or aminophenyl, wherein the amino of the latter three groups can be substituted with
   (a) Ar;
   (b) Ar—Z—, Ar-alkyl-Z—, Ar—Z-alkyl, Ar-amino-Z—, Ar-aminoalkyl-Z—, or Ar-oxyalkyl-Z—, wherein Z is a carbonyl or —$SO_2$—; or
   (c) formyl or alkanoyl.

6. The method of claim 1, comprising administering an effective amount of a compound of the formula I, wherein the compound is selected from the group consisting of thiazole, 2-amino-4-chlorobenzothiazole, 2,4,5-trimethylthiazole, 2-(3,5-dimethylphenoxy)-N-thiazol-2-yl) acetamide, 2-isobutylthiazole, (4-fluorophenyl)thiazolin-2-ylamine, 2-furyl-N-[4-(6-methylbenzothiazol-2-yl)phenyl] carboxamide, and 5,5-dimethyl-2-(2-naphthylamino)-4,5,6-trihydrobenzothiazol-7-one.

7. The method of claim 1, comprising administering an effective amount of a compound of the formula I, wherein
   d. $R^a$ and $R^b$ are
      1. independently selected from hydrogen, acylamino, alkanoyl, alkanoylalkyl, alkoxy, alkoxycarbonyl, alkoxycarbonylalkyl, alkyl, alkylamino, amino, ω-alkylenesulfonic acid, carbamoyl, carboxy, carboxyalkyl (which alkyl can be substituted with alkyloxyimino), cycloalkyl, dialkylamino, halo, hydroxy, (C2–C6)hydroxyalkyl, mercapto, nitro, sulfamoyl, sulfonic acid, alkylsulfonyl, alkylsulfinyl, alkylthio, trifluoromethyl, morpholin-4-yl, thiomorpholin-4-yl, piperidin-1-yl, 4-[$C_6$ or $C_{10}$] arylpiperidin-1-yl, 4-[$C_6$ or $C_{10}$]arylpiperazin-1-yl, Ar {wherein, consistent with the rules of aromaticity, Ar is $C_6$ or $C_{10}$ aryl or a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, each heteroaryl ring can be fused to a substituted benzene, pyridine, pyrimidine, pyrazine, pyridazine, or (1,2,3)triazine (wherein the ring fusion is at a carbon-carbon double bond of Ar)}, Ar-alkyl, ArO—, Ar$SO_2$—, ArSO—, ArS—, Ar$SO_2$NH—, ArNH, (N—Ar)(N-alkyl)N—, ArC(O)—, ArC(O)NH—, ArNH—C(O)—, and (N—Ar)(N-alkyl)N—C(O)—; or
      2. together with their ring carbons form a $C_6$- or $C_{10}$-aryl fused ring; or
      3. together with their ring carbons form a $C_5$–$C_7$ fused cycloalkyl ring having no double bonds except any fused double bond of the formula I or IA ring, which cycloalkyl ring can be substituted by one or more of the group consisting of alkyl, amino, aminocarbonyl, carboxy, fluoro, or oxo, where multiple substituents are located on different carbon atoms of the cycloalkyl ring, except in the case of alkyl and fluoro substituents, which can be located on the same or different carbon atoms; or
      4. Altogether with their ring carbons form a fused 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N; or
      5. together with their ring carbons form a fused five to six membered second heterocycle, wherein the fused heterocycle consists of ring atoms selected from the group consisting of carbon, nitrogen, oxygen, sulfur, and $S(O)_n$, wherein n is 1 or 2,
         wherein aryl, Ar, or Ar$^\Phi$ can be substituted with, in addition to any substitutions specifically noted one or more substituents selected from the group of alkyl, amino, dialkylamino, 1-pyrrolidinyl, 4-[C6 or C10]arylpiperazin-1-yl, 4-[C6 or C10] arylpiperidin-1-yl, azetidin-1-yl, morpholin-4-yl, thiomorpholin-4-yl, piperazin-1-yl, piperidin-1-yl; and
         heterocycles, except those of Ar and Ar$^\Phi$, can be substituted with in addition to any substitutions specifically noted one or more substituents selected from acylamino, alkanoyl, alkoxy, alkoxycarbonyl, alkoxycarbonylalkyl, alkyl, (C1 to C3)alkylenedioxy, alkylamino, alkylsulfonyl, alkylsulfinyl, alkylthio, amino, ArC(O)—, ArO—, Ar—, Ar-alkyl, carboxy, dialkylamino, fluoro, fluoroalkyl, difluoroalkyl, hydroxy, mercapto, oxo, sulfamoyl, trifluoromethyl, 4-[$C_6$ or $C_{10}$] arylpiperidin-1-yl and 4-[$C_6$ or $C_{10}$]arylpiperazin-1-yl, wherein multiple substituents are located on different atoms of the heterocyclic ring, with the proviso that alkyl, alkoxycarbonyl, and fluoro substituents can be substituted on the same carbon atom of the heterocyclic ring.

8. The method of treating or ameliorating of claim 1, comprising treating or ameliorating stiff vessel disease, peripheral vascular disease, coronary heart disease, stroke, myocardial infarct, cardiomyopathies, restenosis, hypertension, isolated systolic hypertension, heart failure, or sickle cell anemia.

9. The method of treating or ameliorating of claim 1, comprising treating or ameliorating diabetes or its associated adverse sequelae, peripheral neuropathy, tissue damage caused by dialysis, diabetic nephropathy, or end stage renal disease.

10. The method of treating or ameliorating of claim 1, comprising treating or ameliorating certain fibrotic diseases, arteriosclerosis, atherosclerosis, rheumatoid arthritis, osteoarthritis, osteorporeosis, limited joint mobility, carpal tunnel syndrome, or periodontal disease.

11. The method of treating or ameliorating of claim 1, comprising treating or ameliorating Alzheimer's disease or amyotrophic lateral sclerosis (ALS).

12. The method of treating or ameliorating of claim 1, comprising treating or ameliorating macular degeneration, retinopathy, cataracts, or other damage to lens proteins.

13. The method of treating or ameliorating of claim 1, comprising treating or ameliorating asthma.

14. The method of treating or ameliorating of claim 1, comprising treating or ameliorating loss of bladder elasticity, or erectile dysfunction.

15. The method of treating or ameliorating of claim 1, comprising treating or ameliorating wrinkles in skin.

16. The method of treating or ameliorating of claim 1, comprising treating or ameliorating growth of neoplasms.

* * * * *